US00PP29790P3

(12) United States Plant Patent
Tate

(10) Patent No.: US PP29,790 P3
(45) Date of Patent: Nov. 6, 2018

(54) ***PERSEA* PLANT NAMED 'PREMERO'**

(50) Latin Name: *Persea americana*
Varietal Denomination: Premero

(71) Applicant: David Frank Tate, Korora (AU)

(72) Inventor: David Frank Tate, Korora (AU)

( * ) Notice: Subject to any disclaimer, the term of this patent is extended or adjusted under 35 U.S.C. 154(b) by 0 days.

(21) Appl. No.: 15/530,253

(22) Filed: Dec. 15, 2016

(65) Prior Publication Data

US 2017/0172035 P1 Jun. 15, 2017

(30) Foreign Application Priority Data

Dec. 15, 2015 (AU) ..... PBR 2015/342

(51) Int. Cl.
*A01H 5/08* (2018.01)

(52) U.S. Cl.
USPC ..... Plt./200

(58) Field of Classification Search
USPC ..... Plt./200
See application file for complete search history.

*Primary Examiner* — Susan McCormick Ewoldt
(74) *Attorney, Agent, or Firm* — Samuel R. McCoy, Jr.

(57) ABSTRACT

A new and distinct *Persea* cultivar named 'Premero' which is characterized by the combination of precocious fruiting, high fruit yield, fruit with firm flesh and a distinct nutty flavor, and the stability of these characteristics from generation to generation.

5 Drawing Sheets

Latin name of the genus and species: The Latin name of the genus and species of the novel variety disclosed herein is *Persea americana.*

Variety denomination: The inventive cultivar of *Persea* disclosed herein has been given the variety denomination 'Premero'.

CROSS REFERENCE TO RELATED APPLICATIONS

This application claims priority to the Australian Plant Breeders Rights application number 2015/342, filed on Dec. 15, 2015, which is herein incorporated by reference.

BACKGROUND OF THE INVENTION

Parentage: 'Premero' is a seedling selection, presumed to be the result of open pollination of *Persea americana* 'Fuerte' and *Persea americana* 'Hass'. The inventor harvested seeds from an isolated orchard of 'Fuerte' and 'Hass' trees, and subsequently planted the seeds in a field in Korora, New South Wales, Australia. The inventor's goal was to select seedlings from these progeny seedlings which exhibited desirable commercial traits or traits improved over the parent varieties which could then be topworked on mature rootstock for further evaluation for commercial potential. In the spring of 2008, one seedling was observed to flower and fruit much earlier than other progeny seedlings and the parent plants. The fruit of this seedling ripened in early autumn and was found to have a distinct nutty flavor. After further evaluation, the claimed plant was finally selected in March of 2010 was given the name 'Premero'.

Asexual Reproduction: Asexual reproduction of 'Premero', by way of budding, was first performed in summer of 2009 in Korora, New South Wales, Australia. Through four subsequent generations, the unique features of this cultivar have proven to be stable and true to type.

SUMMARY OF THE INVENTION

The cultivar 'Premero' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Premero'. These characteristics in combination distinguish 'Premero' as a new and distinct *Persea americana* cultivar:

1. *Persea* 'Premero' exhibits precocious fruiting, setting fruit very early in the growing season; and
2. *Persea* 'Premero' exhibits a high fruit yield; and
3. *Persea* 'Premero' exhibits fruit with firm flesh and a distinct nutty flavor.

BOTANICAL DESCRIPTION OF THE PLANT

Figure 1:
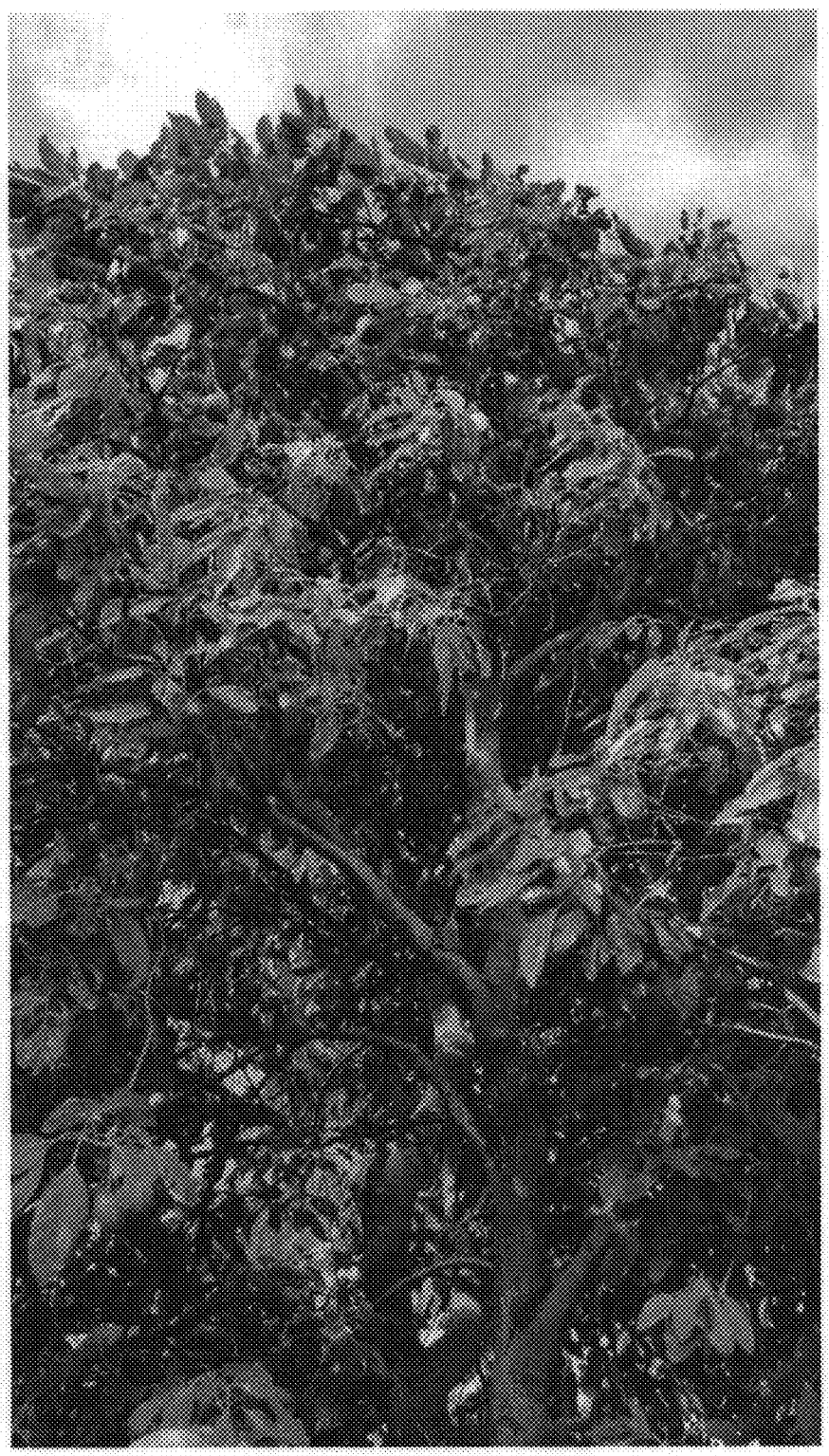
FIG. 1 illustrates, as nearly true as it is reasonably possible to make the same in color photographs of this type, the branching habit of an exemplary 7 year old field-grown 'Premero' plant in Korora, New South Wales, Australia.
Figure 2:
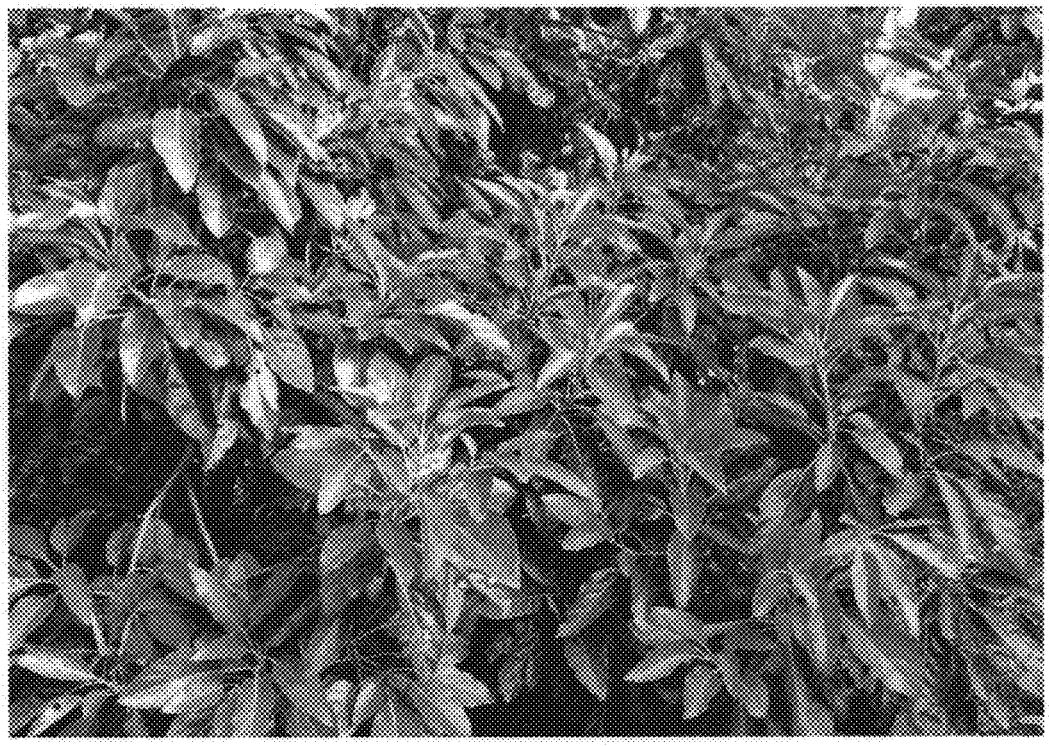
FIG. 2 illustrates, as nearly true as it is reasonably possible to make the same in color photographs of this type, the typical mature foliage of an exemplary 7 year old field-grown 'Premero' plant in Korora, New South Wales, Australia.
Figure 3:
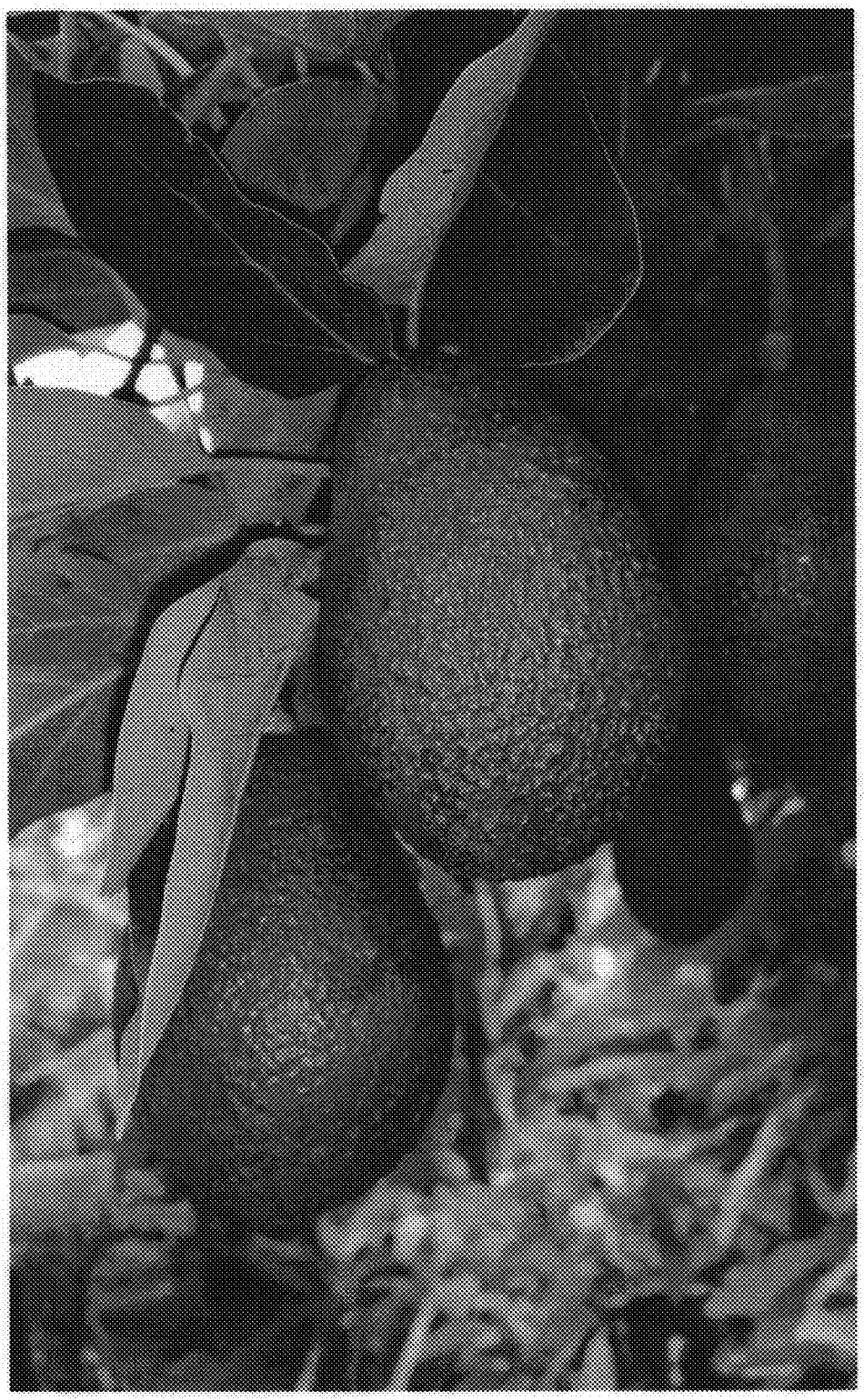
FIG. 3 illustrates, as nearly true as it is reasonably possible to make the same in color photographs of this type, the immature fruit of 'Premero'.
Figure 4:
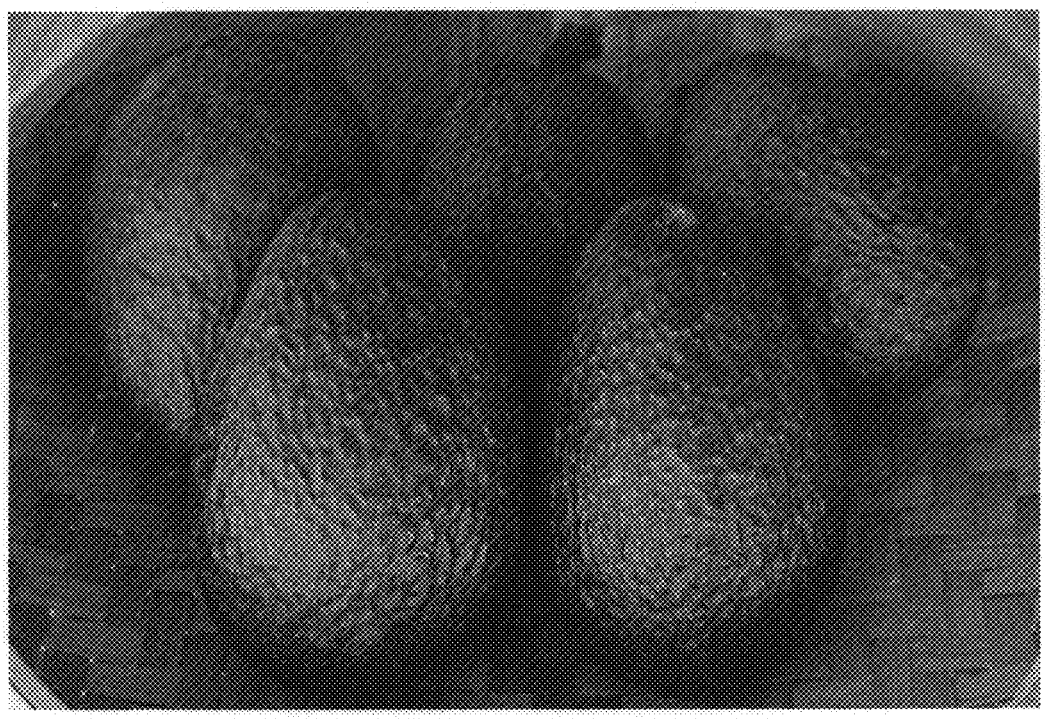
FIG. 4 illustrates, as nearly true as it is reasonably possible to make the same in color photographs of this type, the mature fruit of 'Premero'.
Figure 5:
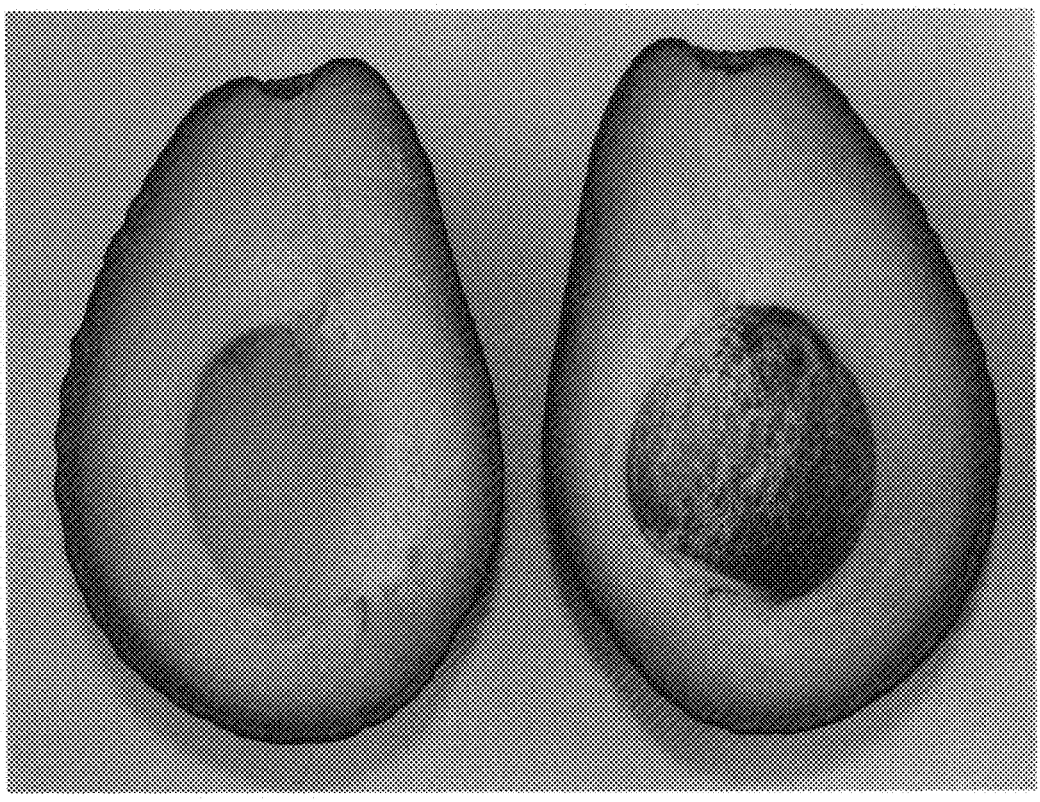
FIG. 5 illustrates, as nearly true as it is reasonably possible to make the same in color photographs of this type, a cross section of the mature fruit of 'Premero'.

With the exception of the fruit description, the following observations and measurements were made in October of 2015 and describe a 7 year old grafted, field-grown 'Premero' plant on 'Velvick' seedling rootstock, grown plant in Korora, New South Wales, Australia. The fruit description was made in February of 2016 from this same tree. The tree was grown in full sun and subsists on natural rainfall and occasional soil supplementation with organic fertilizer. No chemical treatments of any kind were utilized.

Those skilled in the art will appreciate that certain characteristics will vary with older or, conversely, with younger plants. 'Premero' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition.

A botanical description of 'Premero' and comparisons with the parent plants and most similar commercial *Persea* cultivar known to the inventor are provided below.

Plant description:

*Growth habit*.—Freely branching tree.

*Plant shape*.—Rounded.

*Average height from base to top of foliage*.—Approximately 8 m.

*Average width*.—Approximately 10 m.

*Plant vigor*.—Vigorous.

*Propagation details*.—Asexual propagation is accomplished by grafting buds onto rootstock. The most commonly used rootstock is 'Velvick'.

*Time to produce a marketable starter plant*.—Rootstock will form a union with the grafted bud in approximately 4 weeks and be ready for market in approximately 1 year.

*Disease and pest resistance or susceptibility*.—Neither tolerance nor resistance to normal diseases and pests of *Persea americana* have been observed.

*Environmental tolerances*.—Hardy to approximately 0 degrees Celsius.

Root system:

*General*.—Taproot.

*Distribution in the soil profile*.—Shallow to moderately deep.

*Texture*.—Smooth; glabrous.

Stems:

*Branching habit*.—Single rootstock leader with reticulate lateral branches above the graft union; freely-branched.

*Number of lateral branches per plant*.—50.

*Appearance and shape*.—Rounded.

*Length of lateral branches*.—10.2 cm.

*Diameter of fruiting branches*.—Averaging 1.5 cm at the widest point.

*Internode length on lateral branches*.—1.0 cm.

*Texture*.—Smooth.

*Aspect*.—Upward and outward.

*Strength*.—Moderately strong to strong.

*Color, juvenile*.—Yellow-green, RHS 154A.

*Color, mature*.—Green, slightly darker than RHS 143A.

*Pubescence*.—Glabrous.

Foliage:

*Arrangement*.—Alternate to spiraled.

*Attachment*.—Petiolate.

*Division*.—Simple.

*Lamina*.—Dimensions — 17.0 cm long, 9.5 cm wide, and 0.5 mm thick. Shape — Ovate. Aspect — Slightly carinate. Apex — Acute. Base — Obtuse. Margin — Entire; slightly sinuate. Pubescence, adaxial surface — Glabrous. Texture and luster of adaxial surface — Smooth and glossy. Pubescence, abaxial surface — Glabrous. Texture and luster of abaxial surface — Smooth and matte. Color — Juvenile foliage, adaxial surface — Yellow-green, RHS N144C. Juvenile foliage, abaxial surface — Yellow-green, RHS 145B. Mature foliage, adaxial surface — Green, RHS 139B. Mature foliage, abaxial surface — Green, RHS N138D. Venation — Pattern — Reticulate. Color, adaxial surface — Yellow-green, RHS N144C. Color, abaxial surface — Yellow-green, RHS N144C.

*Petiole*.—Length — 4.0 cm. Width — 0.3 cm. Texture — Glabrous; smooth. Strength — Strong. Color — Yellow-green, RHS 144C.

Inflorescence:

*Type*.—Terminal panicle.

*Natural flowering season*.—Spring in Korora, New South Wales, Australia.

*Flowering habit*.—Some recurrent blooming on same panicle.

*Inflorescence dimensions*.—Up to 200 mm long and 150 mm across.

*Inflorescence quantity*.—Abundant; one panicle potentially occurring at the end of every lateral branch.

*Quantity of flowers per inflorescence*.—Approximately 40.

*Peduncle*.—Dimensions — 120 mm long and 8.0 mm in diameter at the base. Color — A mixture of yellow, RHS 10D, and yellow-green, RHS N144C. Texture and luster of lateral branches — Glabrous, smooth and moderately glossy. Strength — Moderately strong.

*Pedicels*.—Dimensions — 10 mm long and 2.0 mm in diameter. Color — Yellow, RHS 10D. Texture and luster — Smooth, glabrous and moderately glossy. Strength — Low. Nail head — Not observed at this time.

Flower buds:

*Bud shape*.—Elliptical.

*Bud dimensions*.—10 mm long and 5.0 mm in diameter.

*Bud color*.—Yellow, RHS 10D.

*Rate of opening*.—Rapid.

Flower:

*Flower type*.—Perfect; simple.

*Flower shape*.—Star.

*Persistence*.—Not persistent.

*Flower aspect*.—Erect to horizontal.

*Fragrance*.—Not noted.

*Dimensions*.—Approximately 2.5 cm in diameter and 2.0 cm tall.

*Tepals*.—Arrangement — Rotate; tepals arranged in a single whorl. Quantity — 6. Fused or unfused — Unfused. Petal dimensions — Approximately 10 mm long and 5.0 mm wide. Shape — Narrow ovate. Apex — Acute. Base — Obtuse. Margin — Entire; not undulated. Texture — Finely pubescent. Color when opening (upper side) — Yellow, RHS 10D. Color when opening (under side) — Yellow, RHS 10D. Color when fully opened (upper side) — Yellow, RHS 10D. Color when fully opened (under side) — Yellow, RHS 10D. Color fading to — Not fading.

Reproductive organs:

*Androecium*.—Stamen quantity — 9. Filament — Dimensions — Approximately 5.0 mm long and approximately 0.5 mm in diameter. Color — Yellow, RHS 10D. Anther — Anther attachment — Basifixed. Anther shape — Oblong; 4-celled. Anther size — 4.0 mm long and 1.5 mm in diameter. Anther color — Yellow, RHS 10D. Pollen — Amount of pollen — Low. Pollen color — Yellow, RHS 10D.

*Gynoecium*.—Pistil quantity — One. Stigma — Shape — Round. Dimensions — Approximately 0.75 mm across and 0.75 mm tall. Color — Yellow, RHS 10D. Style — Dimensions — 7 mm long and 0.5 mm in diameter. Color — Yellow, RHS 10D. Ovary — Position — Superior. Shape — Globose. Diameter — 2 mm. Color — Yellow, RHS 10D.

Seed and fruit:

*Fruit*.—Type — Single seeded berry Shape — Pear shaped being broader at the base. Dimensions — 75 mm in diameter and 120 mm long. Weight — 230 grams, on average. Texture — Rough. Color, skin — Beginning as a green, nearest to RHS146A, and maturing to red-purple, nearest to RHS 187A. Color, flesh — Light yellow, towards the seed, nearest to RHS 11B, and transitioning to green towards the skin, nearest to RHS 143A. Productivity of the fruit — A 5 year old tree will produce approximately 55 to 60 pounds of fruit. Storage characteristics — Fruit stored for 15 days at 4 degrees Celsius show no signs of internal breakdown or ripening.

*Seed*.—Quantity — One. Shape — Ovoid. Size — 40 mm in diameter and 37.5 mm long. Color — Testa color 169A. Texture and luster — Smooth and matte.

COMPARISON WITH THE PARENT PLANTS

Plants of the new cultivar 'Premero' may be distinguished from the first presumed parent, *Persea americana* 'Fuerte' (not patented), by the characteristics described in Table 1.

TABLE 1

| Characteristic | 'Premero' | 'Fuerte' |
|---|---|---|
| Skin of mature fruit; general coloration. | Maroon. | Green. |
| Skin of mature fruit; thickness. | 2.5 to 3.0 mm. | 1.5 to 2.0 mm. |
| Flesh of mature fruit; general coloration. | Yellow. | Cream. |
| Fruit flavor. | Distinct nutty flavor. | Very mild avocado. |
| Firmness of the fruit flesh. | Firm. | Light. |
| Skin of mature fruit; general coloration. | Maroon. | Green. |

Plants of the new cultivar 'Premero' may be distinguished from the second presumed parent, *Persea americana* 'Hass' (not patented), by the characteristics described in Table 2.

TABLE 2

| Characteristic | 'Premero' | 'Hass' |
|---|---|---|
| Shape of the mature fruit. | More elongated; distal end is indented. | Classical oval; distal end is rounded. |
| Size of seed. | Smaller than 'Hass'. | Larger than 'Premero'. |
| Time of fruit ripening. | Very early to early season. | Mid to late season. |

COMPARISON WITH THE CLOSEST KNOWN COMMERCIAL VARIETY

Plants of the new cultivar 'Premero' may be distinguished from the commercial variety, *Persea* 'Shepard' (not patented), which is also a precocious fruiting variety, by the characteristics described in Table 3.

TABLE 3

| Characteristic | 'Premero' | 'Shepard' |
|---|---|---|
| Skin of mature fruit; general coloration. | Maroon. | Green. |
| Skin of mature fruit; thickness. | 2.5 to 3.0 mm. | 1.5 to 2.0 mm. |
| Flesh of mature fruit; general coloration. | Yellow. | Cream. |
| Fruit flavor. | Distinct nutty flavor. | Mild avocado. |
| Firmness of the fruit flesh. | Firm. | Light. |

That which is claimed is:

1. A new and distinct cultivar of *Persea* plant named 'Premero', substantially as described and illustrated herein.

* * * * *